United States Patent [19]
Mavrovic

[11] 4,088,685
[45] May 9, 1978

[54] UREA SYNTHESIS WITH IMPROVED HEAT RECOVERY AND CONVERSION

[76] Inventor: Ivo Mavrovic, 530 E. 72nd St., New York, N.Y. 10021

[21] Appl. No.: 725,444

[22] Filed: Sep. 22, 1976

Related U.S. Application Data

[62] Division of Ser. No. 650,973, Jan. 21, 1976, which is a division of Ser. No. 190,519, Oct. 19, 1971, Pat. No. 3,952,055.

[51] Int. Cl.$^2$ .......................................... C07C 126/02
[52] U.S. Cl. ................................................ 260/555 A
[58] Field of Search ............. 260/555 A; 23/260, 290; 165/2, 61, 105

[56] References Cited
U.S. PATENT DOCUMENTS 3,072,721  1/1963  Grossmann ...................... 260/555 A

OTHER PUBLICATIONS

Kirk-Othmer, Encyclopedia of Chemical Technology, vol. 21, 1970, pp. 37-51.

*Primary Examiner*—Edward J. Meros
*Attorney, Agent, or Firm*—Flynn & Frishauf

[57] ABSTRACT

Heat recovery and conversion of reactants to urea are improved in adiabatic and in isothermal urea synthesis systems. Ammonia, carbon dioxide and ammonium carbamate feed streams are charged to the lower portion of a reactor, which has indirect heat exchange means positioned therein extending from the lower portion to the upper portion and which includes a heat exchange medium. Said means has a first header positioned in said upper portion, a second header positioned in the lower portion, and conduit means interconnecting the headers for passing the medium therebetween. Heat of reaction of the feed streams is imparted to the medium in the second header. The resulting reaction mixture is passed to the upper reactor portion, as is the heated medium to the first header, with heat of the medium being transferred to the reaction mixture as it is so passed.

7 Claims, 6 Drawing Figures

UREA SYNTHESIS WITH IMPROVED HEAT RECOVERY AND CONVERSION

RELATED APPLICATIONS

This application is a division of application Ser. No. 650,973, filed Jan. 21, 1976, which, in turn, is a division of application Ser. No. 190,519, filed Oct. 19, 1971 and now U.S. Pat. No. 3,952,055.

This application is also related to my applications Ser. Nos. 725,442 and 725,443, also filed Sept. 22, 1976.

FIELD OF THE INVENTION

This invention relates to the synthesis of urea from $NH_3$ and $CO_2$. More specifically, it relates to a new method of removing heat from an exothermic urea synthesis reactor operating in the pressure range from 130 to 400 $Kg/cm^2$, in the temperature range from 160° to 220° C, in an $NH_3$ to $CO_2$ overall reactor feed mol ratio from 2.8 to 7 to one and in a $H_2O$ to $CO_2$ overall reactor feed mol ratio from zero to 1.5 to one. It also relates to a new method of increasing the conversion in the reactor.

BACKGROUND OF THE INVENTION

Urea is generally produced by the well known method of contacting $NH_3$ and $CO_2$ to form ammonium carbonate and of dehydrating the latter to urea. The first reaction is instantaneous and substantially complete; the second one is much slower and incomplete, and it takes place only in the liquid phase. It is also known that in the presence of excess $NH_3$ the conversion of ammonium carbamate to urea is promoted, and that in the presence of excess water it is hindered.

The formation of ammonium carbamate is strongly exothermic, and the dehydration of ammonium carbamate to urea is endothermic, but to a lesser degree. For this reason, generally excess heat must be removed from the urea synthesis reactor if the formation of ammonium carbamate and the dehydration of carbamate to urea are simultaneously carried out in the same vessel.

The excess exothermic heat of reaction is usually removed from the urea synthesis reactor by producing steam in a coil immersed in the urea synthesis mixture. The common drawbacks of such a method of removal of the excess heat of reaction from a urea synthesis reactor are as follows: 1. a relatively large reactor coil is usually required due to the small temperature differential normally available between the synthesis reactor mixture and the boiling condensate in the reactor coil. This problem becomes very much pronounced in the case that steam must be produced in the reactor coil at a relatively high and usable level and at the same time the reactor is operated at a relatively high $NH_3$ to $CO_2$ reactor feed mol ratio, for instance above about 3.4 to one. It is a well known fact that, in the presence of excess $NH_3$ in the urea synthesis reaction mixture, the vapor pressure of the reaction mixture is increased and its boiling point is decreased, thus requiring a lower reactor operating temperature when operating at a predetermined and constant reactor pressure level. 2. Local overheating of the urea synthesis reaction mixture occurs due to poor heat transfer rate to the coil, with consequent vaporizing of the reactants $NH_3$ and $CO_2$, and consequent loss in conversion of ammonium carbamate to urea.

There are two specific cases in which the reactor coil usually is not required because of the fact that the excess exothermic heat available in the urea synthesis reactor is absorbed by a relatively large amount of either excess $NH_3$ or carbamate recycle solution or both, fed to the urea synthesis reactor at a relatively lower temperature. For example, in the so called "ONCE-THROUGH Urea Synthesis Processes", the unconverted reactants present in the reactor effluent are not recycled back to the reactor, but they are separated as gas from the aqueous urea product solution by steam heating at reduced pressure and are sent to an adjacent plant for recovery and for the production of either ammonium sulfate or ammonium nitrate. In such Once Through Processes the amount of Liquid $NH_3$ reactor feed can be increased in practice to the point at which all the excess exothermic heat available in the urea synthesis reactor is used internally for the heating of the excess liquid $NH_3$ reactor feed stream to the reactor operating temperature inside the reactor. Customarily, in this case the liquid $NH_3$ reactor feed and the reactor operating temperature are maintained, respectively, at about 20° C. and about 180°–185° C.

Furthermore, in the so called "Partial or Total Carbamate Solution Recycle Urea Synthesis Processes", the above-mentioned unconverted reactants separated from the aqueous urea product solution in the form of a gaseous mixture, instead of being used for the production of ammonium sulfate or nitrate, are absorbed in water to form an ammoniacal aqueous solution of ammonium carbamate, and are recycled into the urea synthesis reactor partially or totally, at a usual temperature of about 90°–100° C. In this latter case, the excess exothermic heat available in the reactor is used internally to elevate the temperature of the carbamate solution recycle stream from 90°–100° C. to the above-mentioned reactor operating temperature of 180°–185° C. Obviously in such a case, if the amount of recycled carbamate solution is relatively large, the corresponding amount of heat in deficiency must be added to the reactor if one wishes to maintain its operating temperature at a certain optimum and desired temperature level. This amount of heat in deficiency is usually added to the reactor by preheating the relatively cold liquid $NH_3$ reactor feed stream from the above-mentioned temperature of about 20° C. to 80° C. There is a common drawback to both such specific cases with respect to the conversion in the reactor, as will be explained below.

As discussed above, it becomes evident that in both cases, either in a Once Through or in a Carbamate Solution Recycle urea synthesis process, the exothermic heat of reaction available in the urea synthesis reactor is wasted by being used internally for the sole purpose of bringing the relatively colder reactor feed streams up to the operating temperature at which the urea synthesis reactor is maintained. Therefore, such a reactor runs completely adiabatically, without heat removal or heat addition, once the reactor feed streams are introduced into the reactor. However, if the relatively colder reactor feed streams are preheated beyond the point at which a urea synthesis reactor operates adiabatically, as for instance in accordance with the method described in U.S. Pat. No. 3,579,636, it becomes necessary to remove from the reactor the equivalent amount of heat added to the reactor feed streams in excess of the normal requirement of an adiabatic reactor. In such a case, the urea synthesis reactor becomes exothermic again, as for instance in the case of the above mentioned Once Through urea synthesis processes.

As mentioned above, the problem of removing heat from the urea synthesis reactor becomes more complicated when excess $NH_3$ is used in the reactor for the purpose of attaining a higher degree of conversion of ammonium carbamate to urea.

It has been found that by removing the excess heat of reaction, available in an exothermic reactor, in an external high pressure heat exchanger substantially operating at the same reactor pressure and at a relatively lower $NH_3$ to $CO_2$ molar ratio than the reactor, and that by subsequently contacting the resulting reaction mixture with additional excess $NH_3$ in a substantially adiabatic urea synthesis reactor, considerable advantages are attained, as described further below.

SUMMARY OF THE INVENTION

In accordance with this invention, there is provided a process wherein, the major part or all of the fresh make-up $CO_2$ gas required for the production of urea is mixed with $NH_3$ in an $NH_3$ to $CO_2$ molar ratio of from about 2.2 to about 3.5 to 1, at reactor synthesis pressure, either in the shell side or in the tube side of a conventional shell and tube heat exchanger. A stream containing one or more of the following compounds: water, ammonium carbamate, ammonia and urea can be admixed with the above-mentioned fresh make-up $CO_2$ gas and $NH_3$ mixture. In such a case the overall $NH_3$ to $CO_2$ molar ratio of the total resulting mixture is maintained from about 2.2 to 1 to about 3.5 to 1. The temperature of the total reaction mixture inside the heat exchanger is maintained constant within a range from about 160° to about 220° C. by removing heat from the heat exchanger. Such heat is removed from the heat exchanger either by circulating a relatively colder fluid in indirect contact with the reaction mixture, or by producing steam from condensate in indirect contact with the reaction mixture.

There is also provided a process wherein $NH_3$, $CO_2$ and an aqueous solution comprising ammonium carbamate are contacted at elevated pressure and temperature to form a total urea synthesis mixture in a urea synthesis reactor to form urea. Ammonium, carbon dioxide and ammonium carbamate feed streams are charged to the lower portion of a reactor, which has indirect heat exchange means positioned therein extending from the lower portion to the upper portion and which includes a heat exchange medium. Said means has a first header positioned in said upper portion, a second header positioned in the lower portion, and conduit means interconnecting the headers for passing the medium therebetween. Heat of reaction of the feed streams is imparted to the medium in the second header. The resulting reaction mixture is passed to the upper reactor portion, as is the heated medium to the first header, with heat of the medium being transferred to the reactor mixture as it is so passed.

DRAWINGS

Advantages of the invention will become apparent to those skilled in the art from the following detailed description considered in conjunction with the drawings wherein FIG. 1 is a schematic flow diagram of a urea synthesis reactor system wherein a reactor having a coil positioned therein is associated with a vertical shell and tube heat exchanger. The coil is open proximate the bottom section of the reactor.

SPECIFIC EMBODIMENTS OF THE INVENTION

Figure 1:
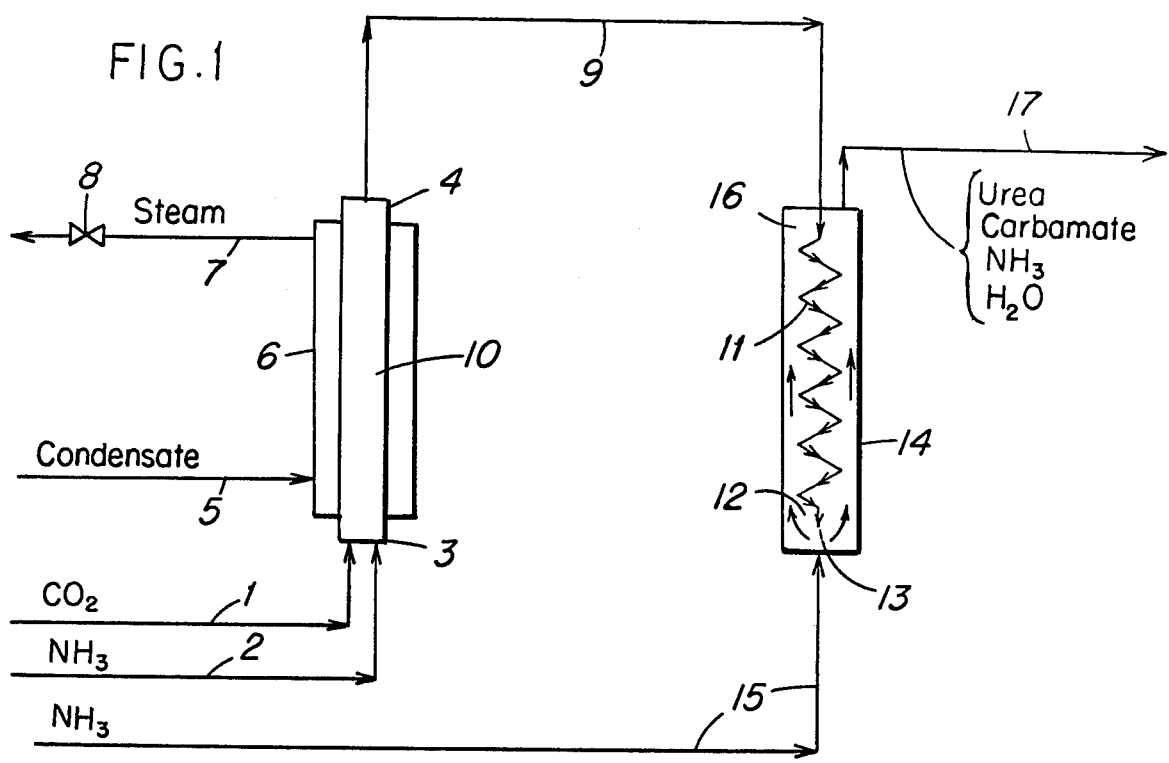

The amount of heat removed from the above-mentioned heat exchanger is controlled by regulating the flow of $NH_3$ to the heat exchanger reaction mixture, and thus by regulating the overall $NH_3$ to $CO_2$ molar ratio in the heat exchanger reaction mixture. According to this new method, in the case of either removal of an excessive amount of heat from the heat exchanger (which fact will cause a drop in temperature of the subsequent adiabatic reactor as will be explained further below) or overheating of the reaction mixture, the feed rate of $NH_3$ admixed to the reaction mixture is increased. As a consequence, due to the increase in free excess $NH_3$ content in the reaction mixture, the vapor pressure of the reaction mixture will increase or the boiling point of the reaction mixture will decrease when operating at a constant pressure level, as mentioned above. As a further consequence, a smaller amount of heat will be transferred to the relatively colder cooling medium circulated through the heat exchanger due to the decrease in temperature differential between the reaction mixture and the cooling medium absorbing heat. In the specific case in which the correct amount of heat is removed from the heat exchanger, but at the same time the temperature of the reaction mixture is too high, an increase in $NH_3$ feed rate to the reaction mixture will cause the temperature of the reaction mixture to drop within the desired temperature range as explained above. In order to restore the heat removal to the correct amount, it will be necessary either to reduce the temperature of the cooling medium absorbing heat or to increase its circulation rate, or to produce lower pressure steam in the heat exchanger if heat is removed by boiling condensate. In either case the removal of the amount of heat will be restored to the correct value, but at a lower reaction mixture operating temperature, as desired.

In the case of removing an insufficient amount of heat from the heat exchanger, which fact will cause an increase in temperature of the subsequent adiabatic reactor as will be explained further below, the feed rate of $NH_3$ admixed to the reaction mixture is decreased, for the purpose of decreasing the free excess $NH_3$ content in the reaction mixture and thus of increasing the boiling point of the reaction mixture. Consequently, the temperature differential between the reaction mixture and the cooling medium absorbing heat will increase as well as the rate of heat removal from the heat exchanger.

Once the required amount of heat is removed from the reaction mixture, the latter is reduced to the thermodynamic state and conditions prevailing in and characteristic of the adiabatic reactor feed streams. The reaction mixture from the heat exchanger is then mixed with additional $NH_3$ for the purpose of increasing the overall $NH_3$ to $CO_2$ molar ratio in the total mixture to from about 2.8 to 1 to about 7 to 1, and is fed into an adiabatic reactor for conversion of ammonium carbamate to urea. The reactor temperature is controlled by removing the required amount of heat from the preceding high pressure heat exchanger, very much analogously but in the opposite manner to the conventional methods of preheating the liquid $NH_3$ reactor feed stream of a conventional reactor for the purpose of controlling the temperature of such a conventional adiabatic reactor, as was explained before.

In the process according to this invention, the pressure in the reactor is maintained at the substantially same pressure prevailing in the process side of the high pressure heat exchanger described above.

As mentioned above, there are still some problems that are common to the conventional exothermic or adiabatic reactors designed to operate according to conventional methods used heretofore. Normally, the reactants are fed into the bottom section of such a conventional adiabatic reactor, and the synthesis mixture at completion of reaction is discharged from its top section. Such a conventional exothermic or adiabatic reactor usually consists of a cylindrical vertical vessel with a height-to-diameter ratio of from about 6 to about 20 to 1, for the purpose of approaching as much as possible the ideal and in practice preferred pattern of an upwardly plug type flow of the synthesis mixture through the reactor. But due to the facts mentioned above, according to which the reaction of carbamate dehydration to urea is a slow reaction and is endothermic by about 7,000 Kcal/mole of urea formed, the bottom section of such a conventional adiabatic reactor usually operates at a temperature which is from 10° to 15° C higher than the temperature of the synthesis mixture at completion of the reaction at the exit from the reactor. In a few words, part of the exothermic and instantaneous heat of reaction of ammonium carbamate formation from $NH_3$ and $CO_2$ in the reactor bottom section of a conventional reactor is stored as sensible heat in the synthesis mixture, with a consequent increase in temperature of the synthesis mixture, to be later slowly released to supply the amount of endothermic heat required for the dehydration of ammonium carbamate to urea during the upward flow of the synthesis mixture through the reactor. Such a condition invariably leads in a conventional reactor to undesirable local overheating of the synthesis mixture in the reactor bottom section, with consequent loss of $NH_3$ and $CO_2$ gaseous reactants from the liquid phase of the synthesis mixture, and with consequent decrease in conversion of total $CO_2$ to urea. As a further disadvantage of such a condition prevailing in a conventional reactor, the temperature of the synthesis mixture in the upper portion of the cylindrical reactor decreases in proportion to the amount of urea formed by the endothermic process of carbamate dehydration to urea and water. Due to this gradual drop in temperature of the synthesis mixture during its upward flow through the reactor, the rate of carbamate dehydration to urea is slowed down, with obvious negative effects on the overall conversion of total $CO_2$ present in the synthesis mixture to urea.

Figure 6:
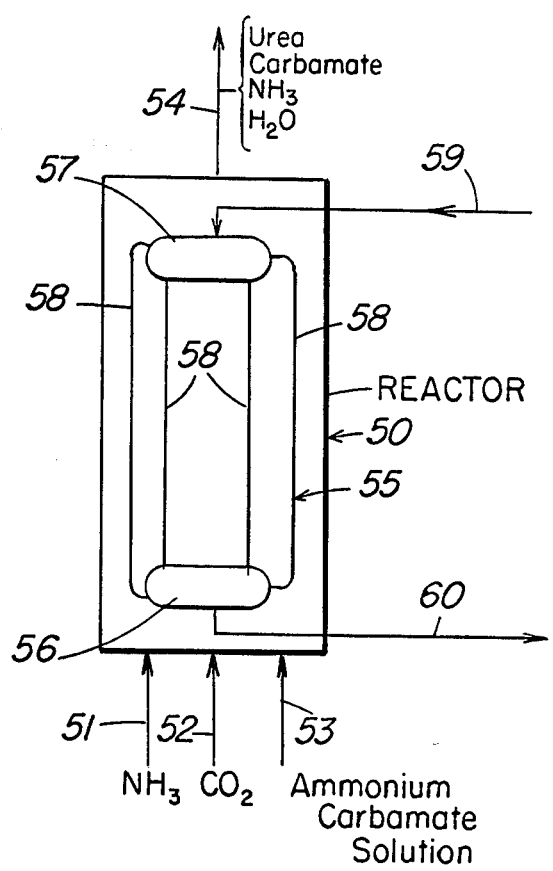
FIG. 6 is a schematic flow diagram of such a system wherein a reactor has a heat exchange means positioned therein, said means comprising separate headers interconnected by conduits.

According to the new methods described herein, either the mixture of the reactor feed streams of the adiabatic reactor are counter-currently contacted in indirect heat exchange with the synthesis mixture; or the reactor feed streams are preheated below the point of attaining the adiabatic temperature equilibrium in the reactor at a certain preferred operating temperature level and the reactor mixture is heated in the reactor; or heat is removed from the bottom section of the reactor and the upper section of the reactor is heated at the same time. In the latter case simultaneous cooling of the bottom section and heating of the upper section of the reactor can be accomplished practically by immersing a coil into the reactor synthesis mixture, by vaporizing condensate in the bottom part of the coil in contact with the relatively hotter synthesis mixture and condensing the steam thus formed in the upper part of the coil in contact with the relatively cooler synthesis mixture. By this method, excess heat from the bottom section of the reactor is transferred to the upper section of the reactor where it is required for the endothermic process of carbamate dehydration to urea. Such a reactor coil can be of the shape of an upper and lower cylindrical or spherical vessel connected with numerous tubes in parallel, wherein condensate is refluxing internally; more exactly it is vaporized in the bottom section and condensed in the upper section of the coil. This type of reactor is illustrated in FIG. 6 and is discussed hereinbelow.

In the second case mentioned above, either the reactor feed streams are preheated below the point of attaining the adiabatic temperature equilibrium in the reactor at a certain preferred and optimum operating temperature, or more heat is removed from the above-described high pressure reactor feed streams to the heat exchanger than is required to bring the reactor temperature down to the preferred optimum operating temperature. In either case, the equivalent amount of such heat subtracted in excess from the reactor or insufficiently supplied to the reactor feed streams must be supplied to the reactor from an external source in order to maintain the reactor temperature at the same preferred optimum level. This is accomplished by feeding steam to a coil immersed into the synthesis mixture and extracting the condensate from the coil. The amount of heat added to such a coil is equivalent to from about 0.1 to about 12,000, preferably from about 2,000 to about 10,000, Kcal/Kg mole of urea formed in the reactor.

In the first case mentioned above, the simplest method of preventing the bottom section of an adiabatic reactor from overheating is to bring the mixture of two or more reactor feed streams into indirect counter-current heat exchange with the reactor synthesis mixture. However, the most economical and practical method of accomplishing said indirect counter-current heat exchange is as follows. A part or the total amount, from about 5 to 100 mol percent, of one or more of the reactor feed streams, namely $CO_2$, $NH_3$ and an ammoniacal aqueous solution of ammonium carbamate which may contain urea, is simultaneously contacted and introduced at the top section of the reactor into a coil which is immersed into the synthesis mixture and runs internally to the reactor, from its top section to its bottom section. The coil immersed into the reactor synthesis mixture is open at its end in the bottom section of the reactor. The mixture of the reactor feed streams in their downward path through the reactor coil releases parts of its heat of reaction and exits from the coil into the bottom section of the reactor. The remaining portion of the reactor feed stream or streams not introduced into the reactor coil is fed to the bottom part of the reactor and mixed with the mixture exiting from the reactor coil. The resulting total mixture rises through the reactor counter-currently to the fluid flowing downwardly inside the reactor coil, and as the dehydration of carbamate to urea progresses with consequent drop in temperature of the reactor synthesis mixture, heat is indirectly transferred from the fluid flowing downwardly through the reactor coil to the urea synthesis mixture flowing upwardly through the reactor.

The reactor synthesis mixture at completion of carbamate dehydration to urea is withdrawn from the top section of the reactor for further processing, not described here.

The following examples serve to illustrate preferred embodiments of this invention.

EXAMPLE 1

A conventional Once Through vertical cylindrical reactor provided with an internal steam coil, is operated at a temperature of about 188° C. and at a pressure of about 270 atmospheres.

4,400 Kg/Hr of $CO_2$ at about 10° C. and 6,800 Kg/Hr of $NH_3$ at about 16° C. are fed to the reactor, in an approximate $NH_3$ to $CO_2$ overall molar ratio of 4 to 1 to yield about 4,200 Kg/Hr of urea, 2,300 Kg/Hr of unconverted ammonium carbamate, 3,400 Kg/Hr of excess $NH_3$ and 1,260 Kg/Hr of water. On this basis, the overall calculated conversion of $CO_2$ to urea is in the order of about 70 percent.

In order to maintain the reactor temperature constant at about 188° C., it is necessary to remove excess heat from the reactor. This is accomplished by producing steam in a reactor coil immersed in the synthesis mixture, at about 9 atmospheres absolute pressure and about 176° C., in an amount of approximately 1,080 Kg/Hr.

The surface area of the reactor coil is approximately equivalent to 64 $m^2$ and the temperature differential available between the reactor synthesis mixture and the boiling condensate producing steam inside the reactor coil is about 11° C.

Referring to FIG. 1, 4,400 Kg/Hr of $CO_2$ at about 10° C. in pipe 1 and 4,420 Kg/Hr of $NH_3$ at about 16° C. in pipe 2 are fed into the bottom section 3 of the tube side of vertical shell and tube heat exchanger 4, operating at about 270 atm. pressure. The overall $NH_3$ to $CO_2$ molar ratio in the feed to heat exchanger 4 is about 2.6 to 1. About 1,000 Kg/Hr of condensate is passed through pipe 5 into the shell side 6 of heat exchanger 4 to produce steam at about 9 atmospheres absolute pressure and about 176° C., which is extracted through pipe 7. The steam pressure in shell side 6 is controlled by means of valve 8 located in steam exit pipe 7.

The temperature of the reaction mixture inside the tubes of heat exchanger 4 is at about 200° C., and thus the temperature differential available between the reaction mixture contained in tubes 10 (not shown) and the boiling condensate contained in shell 6 is about 24° C. The total amount of tube surface area required in heat exchanger 4 is equivalent to about 28 $m^2$, only about 45 percent of the tube surface area required for a conventional reactor coil. The reaction mixture from pipe 9 is passed into reactor coil 11, provided with an open end 12 proximate the bottom section 13 of the reactor 14. The reaction mixture from pipe 9 flows downwardly through coil 11 and is cooled from about 200° to about 180° C. The reaction mixture exits coil 11 at its open end 12 and it is mixed with 2,380 Kg/Hr of ammonia at about 16° C. passed through pipe 15 and introduced into the bottom section 13 of reactor 14, operating at about 270 atmospheres pressure. The resulting synthesis mixture is further cooled below 180° C. due to said mixing of the reaction mixture leaving coil 11 at its end 12 and the relatively colder stream of ammonia in pipe 15. The synthesis mixture, now in a $NH_3$ to $CO_2$ molar ratio of about 4 to 1, flows through the reactor upwardly and in counter-current heat exchange with the relatively hotter reaction mixture flowing downwardly through reactor coil 11. The synthesis mixture is heated to about 188° C. and, at completion of reaction of carbamate conversion to urea, is withdrawn from the upper section 16 of reactor 14 through pipe 17.

The stream flowing through pipe 17 contains 4,560 Kg/Hr of urea, 1,872 Kg/Hr of unconverted ammonium carbamate, 3,400 Kg/Hr of excess $NH_3$ and 1,368 Kg/Hr of water. On this basis, the back calculated conversion of total $CO_2$ to urea is about 76 percent, compared to 70 percent attained in a conventional reactor described above.

EXAMPLE 2

A conventional vertical cylindrical reactor is adiabatically operated in a total recycle urea synthesis process plant at a temperature of about 190° C. and at a pressure of about 220 atmospheres.

3,124 Kg/Hr of $CO_2$ at about 120° C., 5,182 Kg/Hr of $NH_3$ at about 70° C. and 5,246 Kg/Hr of ammonium carbamate recycle solution at about 85° C. are fed to the above-mentioned conventional reactor. The carbamate recycle solution contains 3,276 Kg/Hr of ammonium carbamate, 690 Kg/Hr of $NH_3$ and 1,280 Kg/Hr of water. No reactor cooling or heating is required, thus the reactor operates adiabatically. The overall $NH_3$ to $CO_2$ molar ratio in the reactor is about 3.8 to 1 and the water to $CO_2$ molar ratio is about 0.629 to 1. At completion of reaction, the reactor effluent stream contains 4,200 Kg/Hr of urea, 3,354 Kg/Hr of unconverted ammonium carbamate, 3,458 Kg/Hr of excess $NH_3$ and 2,540 Kg/Hr of water. On this basis, the back calculated conversion of total $CO_2$ to urea is about 62 percent.

Figure 2:
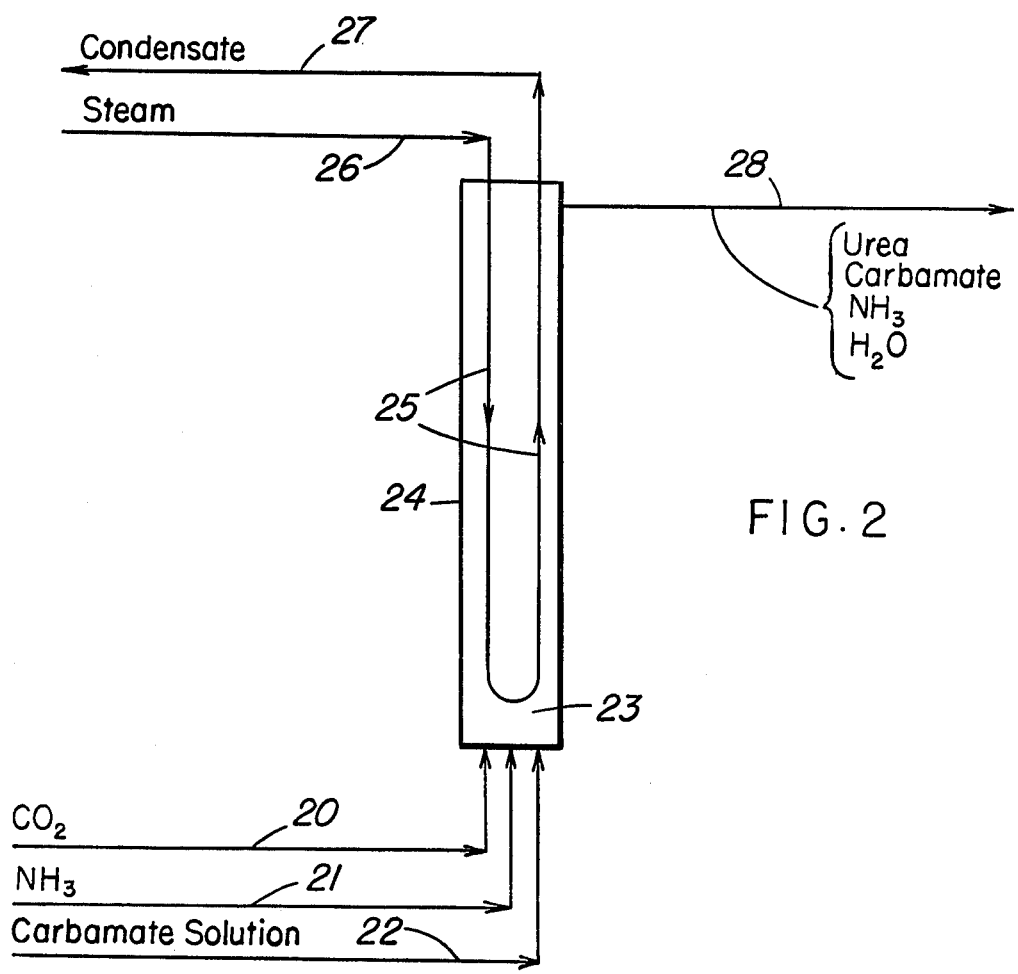
FIG. 2 is a schematic flow diagram of such a system, with a reactor having a heating coil therein.

According to this invention and referring to FIG. 2, 3,124 Kg/Hr of $CO_2$ at about 115° C. in line 20, 4,821 Kg/Hr of $NH_3$ at about 35° C. in line 21 and 4,407 Kg/Hr of ammonium carbamate recycle solution at about 80° C. in line 22 are introduced into the bottom section 23 of vertical cylindrical reactor 24 internally provided with heating coil 25 immersed into the reaction mixture therein. The carbamate solution in line 22 comprises 2,496 Kg/Hr of ammonium carbamate, 745 Kg/Hr of $NH_3$ and 1,166 Kg/Hr of water. Reactor 24 is operated at a pressure of about 220 atmospheres pressure, the $NH_3$ to $CO_2$ overall molar ratio in reactor 24 is about 3.8 to 1, and the water to $CO_2$ molar ratio therein is about 0.629 to 1.

750 Kg/Hr of steam at 16 atmospheres absolute pressure is supplied to reactor heating coil 25 through line 26 for the purpose of maintaining the reactor temperature constant at about 190° C. Condensate is removed from heating coil 25 through line 27. At completion of reaction the reactor effluent is removed from reactor 24 through line 28. The effluent contains 4,200 Kg/Hr of urea, 2,574 Kg/Hr of unconverted ammonium carbamate, 3,152 Kg/Hr of excess $NH_3$ and 2,426 Kg/Hr of water. On this basis, the overall back calculated conversion of total $CO_2$ to urea is about 68 percent compared with the relatively lower conversion of 62 percent attained in the conventional reactor described above, operating at the same $NH_3$ to $CO_2$ and $H_2O$ to $CO_2$ molar ratios.

EXAMPLE 3

A conventional vertical cylindrical reactor is adiabatically operated in a total recycle urea synthesis process plant at a temperature of about 190° C. and at a pressure of about 220 atmospheres. 3,124 Kg/Hr of $CO_2$ at about 120° C., 5,499 Kg/Hr of $NH_3$ at about 75° C., and 4,728 Kg/Hr of ammonium carbamate solution at about 85° C., are fed to the above mentioned conventional reactor. The carbamate recycle solution contains 2,918 Kg/Hr of ammonium carbamate, 600 Kg/Hr of $NH_3$ and 1,210 Kg/Hr of water. No reactor cooling or heating is required, thus the reactor is operated adiabatically. The overall $NH_3$ to $CO_2$ molar ratio in the reactor is about 4.0 to 1 and the water to $CO_2$ molar ratio is about 0.62 to 1. At completion of reaction, the reactor effluent stream contains 4,200 Kg/Hr of urea, 2,996 Kg/Hr of unconverted ammonium carbamate, 3,685 Kg/Hr of excess $NH_3$ and 2,470 Kg/Hr of $H_2O$. On this basis, the back calculated conversion of Total $CO_2$ to urea is about 64 percent.

Figure 3:
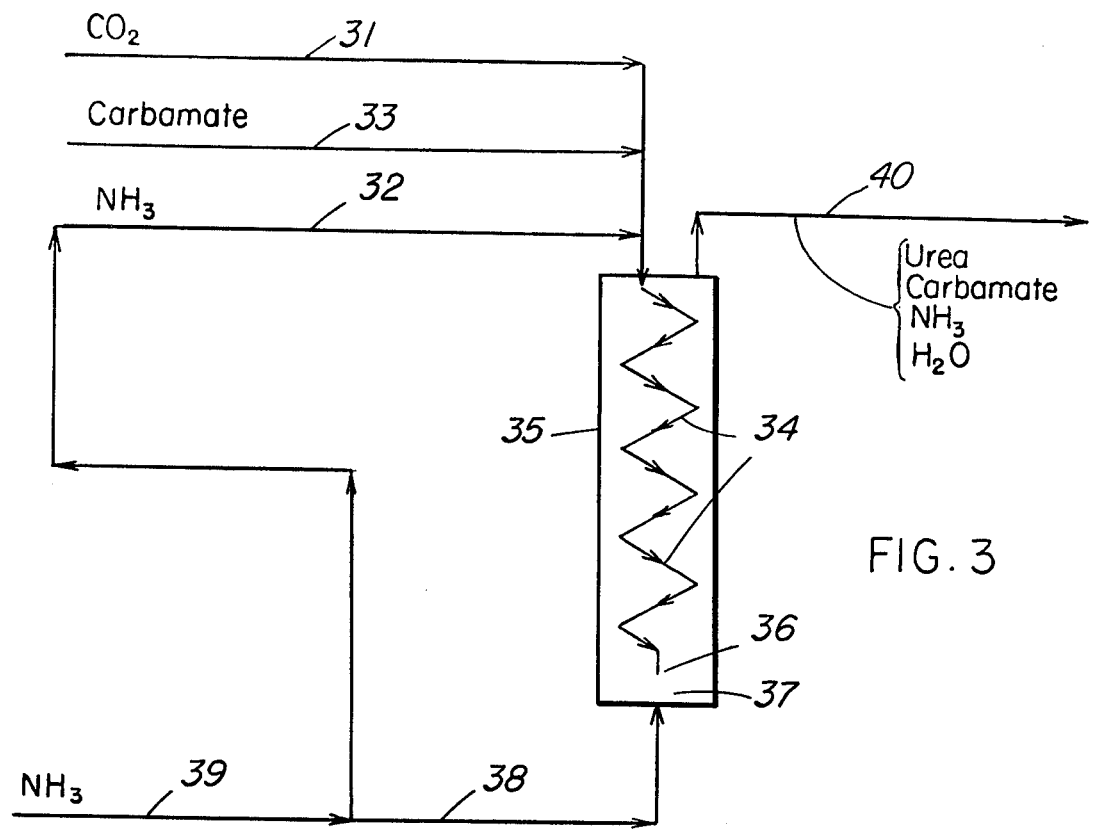
FIG. 3 is a schematic flow diagram of such a system, the reactor thereof being similar to that shown in FIG. 1.

According to this invention and referring to FIG. 3, 3,124 Kg/Hr of $CO_2$ at about 115° C. in line 31, 2,729 Kg/Hr of $NH_3$ at about 46° C. in line 32, and 4,063 Kg/Hr of ammonium carbamate solution at about 80° C. in line 33, are mixed and are introduced into reactor coil 34 inside reactor 35. The overall $NH_3$ to $CO_2$ molar ratio of the mixture in reactor coil 34 is about 2.6 to 1. This mixture flows downwardly through reactor coil 34, leaves reactor 34 at its open end 36 located proximate reactor bottom section 37. The mixture is mixed with 2,400 Kg/Hr of $NH_3$ at about 45° C. which is added to the bottom section 37 of reactor 35 through line 38. The total amount of $NH_3$ fed to the reactor in line 39 is thus equal to 5,129 Kg/Hr and the overall $NH_3$ to $CO_2$ molar ratio in the total resulting reactor mixture in bottom section 37 is about 4.0 to 1, whereas the water to $CO_2$ molar ratio is about 0.62 to 1. Reactor 35 is operated adiabatically at about 190° C. and about 220 atmospheres pressure. No heating or cooling is required, and the reactor temperature is maintained constant at about 190° C. by varying the temperature of one or more of the reactor feed streams 31, 32, 33, 38 or 39, respectively. At completion of reaction, the reactor effluent is removed through overhead line 40. The effluent contains 4,200 Kg/Hr of urea, 2,340 Kg/Hr of unconverted ammonium carbamate, 3,400 Kg/Hr of excess $NH_3$ and 2,376 Kg/Hr of water. Based on this, the back calculated overall conversion of total $CO_2$ to urea is about 70 percent, compared to the relatively lower conversion of 64 percent attained in the conventional reactor described above and operating at the same $NH_3$ to $CO_2$ and $H_2O$ to $CO_2$ molar ratios.

EXAMPLE 4

A conventional vertical cylindrical reactor is adiabatically operated in a total recycle urea synthesis process plant at a temperature of about 188° C. and at a pressure of about 220 atmospheres. 3,124 Kg/Hr of $CO_2$ at about 120° C., 5,928 Kg/Hr of $NH_3$ at about 72° C. and 4,510 Kg/Hr of ammonium carbamate recycle solution at about 88° C., are fed to the above described conventional reactor. The carbamate recycle solution contains 2,730 Kg/Hr of ammonium carbamate, 630 Kg/Hr of $NH_3$ and 1,150 Kg/Hr of water. No reactor cooling or heating is required. The overall $NH_3$ to $CO_2$ molar ratio in the reactor is about 4.3 to 1 and the water to $CO_2$ molar ratio is about 0.60 to 1. At completion of reaction, the reactor effluent stream contains 4,200 Kg/Hr of urea, 2,808 Kg/Hr of unconverted ammonium carbamate, 4,144 Kg/Hr of excess $NH_3$ and 2,410 Kg/Hr of water. On this basis, the calculated conversion of total $CO_2$ to urea is about 66 percent.

Figure 4:
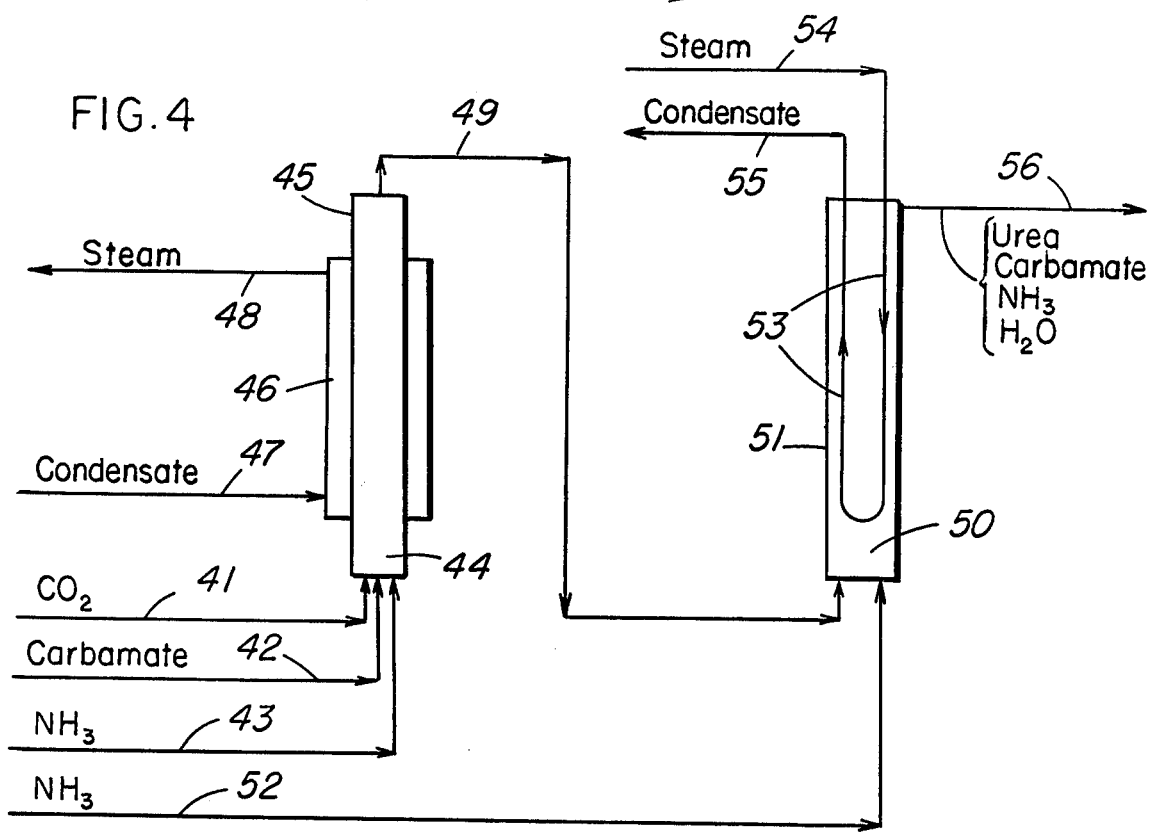
FIG. 4 is a schematic flow diagram of such a system wherein a reactor similar to that shown in FIG. 2 is associated with a vertical shell and tube heat exchanger similar to that shown in FIG. 1.

According to this invention and referring to FIG. 4, 3,124 Kg/Hr of $CO_2$ at about 120° C. in line 41, 3,661 Kg/Hr of carbamate recycle solution at about 120° C. in line 42, and 2,560 Kg/Hr of $NH_3$ at about 120° C. in line 43, are fed to the tube side 44 of vertical shell and tube heat exchanger 45. The carbamate recycle solution in line 42 contains 1,950 Kg/Hr of ammonium carbamate, 670 Kg/Hr of $NH_3$ and 1,041 Kg/Hr of water. The heat of reaction is removed from heat exchanger 45 by producing 1,870 Kg/Hr of steam at about 179° C. and about 9.8 atmospheres absolute pressure in shell side 46 of heat exchanger 45. Condensate is fed to shell side 46 through line 47 and the steam produced is removed through line 48. The reactor mixture leaves heat exchanger 45 at about 200° C. through overhead line 49 in an overall $NH_3$ to $CO_2$ molar ratio of about 2.5 to 1, and is introduced into bottom section 50 of reactor 51. 2,937 Kg/Hr of $NH_3$ at about 120° C in line 52 is also introduced into bottom section 50 and is mixed with the reaction mixture from line 49, so that the total overall $NH_3$ to $CO_2$ molar ratio of the resulting reactor mixture in bottom section 50 is equal to about 4.3 to 1, whereas the water to $CO_2$ molar ratio is about 0.60 to 1. Reactor 51 and tube side 44 of heat exchanger 45 operate at substantially the same pressure of about 220 atmospheres. Reactor 51 is provided with steam coil 53 immersed in the synthesis mixture therein. The temperature inside reactor 51 is maintained constant at about 190° C. by supplying 600 Kg/Hr of steam at about 210° C., and about 18.8 atmospheres absolute pressure to heating coil 53 through line 54. Condensate is extracted from coil 53 through line 55. At completion of reaction, the resulting reaction mixture is extracted from reactor 51 through line 56 located in the upper part of reactor 51. The mixture in line 56 contains 4,200 Kg/Hr of urea, 2,028 Kg/Hr of unconverted ammonium carbamate, 3,753 Kg/Hr of excess $NH_3$ and 2,301 Kg/Hr of water. On this basis, the calculated conversion of total $CO_2$ to urea is about 73 percent, compared to 66 percent conversion attained in the conventional reactor described above and operating at the same $NH_3$ to $CO_2$ molar ratio of 4.3 to 1 and at the same $H_2O$ to $CO_2$ molar ratio of 0.60 to 1.

EXAMPLE 5

Figure 5:
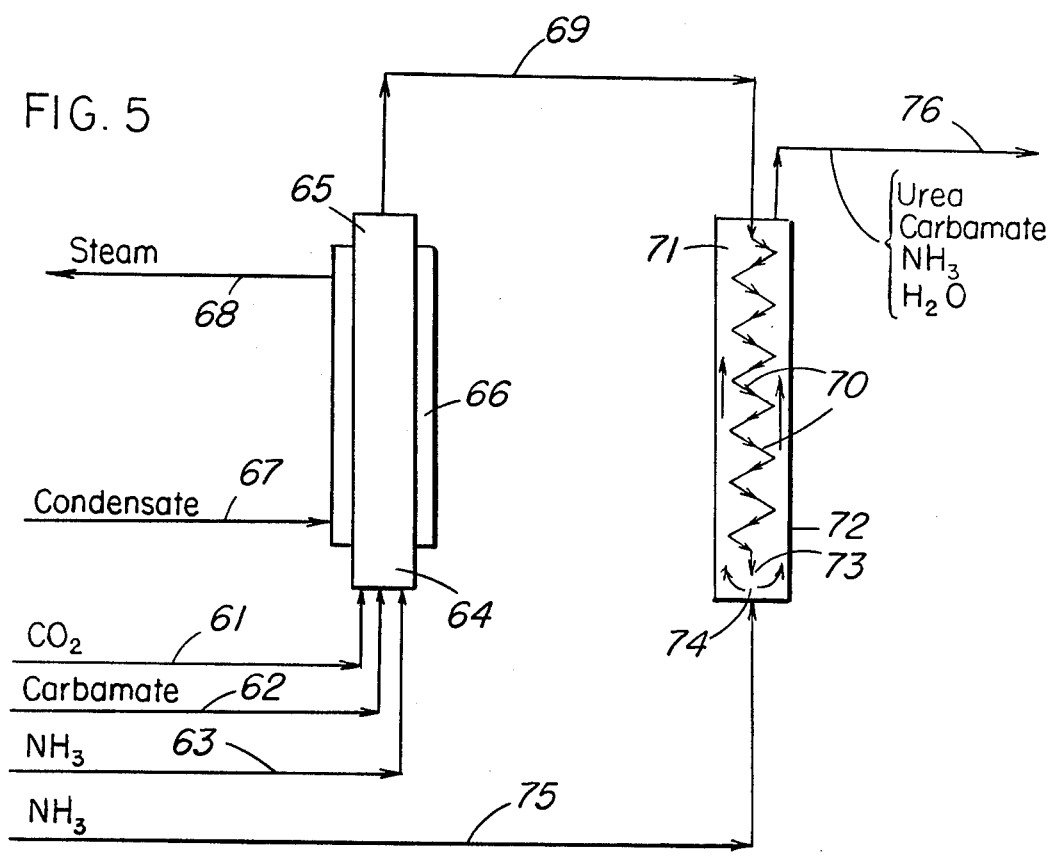
FIG. 5 is a schematic flow diagram of such a system similar to that shown in FIG. 1 but including a conduit for charging ammonium carbamate.

According to this invention and referring to FIG. 5, 3,124 Kg/Hr of $CO_2$ at about 120° C. in line 61, 3,661 Kg/Hr of ammonium carbamate recycle solution at about 120° C. in line 62, and 2,560 Kg/Hr of $NH_3$ at about 120° C. in line 63, are fed to the tube side 64 of vertical shell and tube heat exchanger 65. The carbamate recycle solution in line 62 contains 1,950 Kg/Hr of ammonium carbamte, 670 Kg/Hr of $NH_3$ and 1,041 Kg/Hr of water. The heat of reaction derived from the mixing of said reactor feed streams is removed from heat exchanger 65 by producing 1,250 Kg/Hr of steam at about 179° C. and about 9.8 atmospheres absolute pressure in shell side 66 of heat exchanger 65. Condensate is fed to shell side 66 through line 67 and the steam produced is removed through line 68.

The reaction mixture in tubes 64, at about 220 atmospheres pressure and about 200° C., is removed from heat exchanger 65 through overhead line 69. The reaction mixture has a NH$_3$ to CO$_2$ molar ratio of about 2.5 to 1. Stream 69 is introduced into reactor coil 70 at top section 71 of reactor 72. Reactor coil 70 is immersed into the reactor synthesis mixture and it extends from its top section 71 downwardly to its bottom section 74. Reactor coil 70 is open at its end 73 in reactor bottom section 74. The relatively hotter stream from line 69 flows downwardly through reactor coil 70 and counter-currently to the reactor synthesis mixture which is rising through reactor 72. The reaction mixture leaving coil 70 at its bottom open end 73 is mixed in reactor bottom section 74 with 2,937 Kg/Hr of NH$_3$ at about 120° C. from line 75, so that the overall NH$_3$ to CO$_2$ molar ratio of the reactor synthesis mixture in bottom section 74 and in reactor 72 is about 4.3 to 1, and the H$_2$O to CO$_2$ molar ratio is about 0.60 to 1, similar to Example 4 above.

The reactor synthesis mixture in reactor bottom section 74 is cooled below 185° C. due to mixing with the relatively colder NH$_3$ stream 75 fed to reactor 72, rises through reactor 72 and is heated by indirect heat exchange with the relatively hotter stream 69 flowing counter-currently through reactor coil 70, as explained above. At completion of reaction, the resulting reactor synthesis mixture is withdrawn from reactor top section 71 through overhead line 76 at about 220 atmospheres pressure and about 190° C. The mixture in line 76 contains 4,200 Kg/Hr of urea, 2,028 Kg/Hr of unconverted ammonium carbamate, 3,753 Kg/Hr of excess NH$_3$ and 2,301 Kg/Hr of water. On this basis, the conversion of total CO$_2$ to urea is about 73 percent, compared to 66 percent conversion attained in a conventional reactor described in Example 4 and operating at the same NH$_3$ and H$_2$O to CO$_2$ molar ratios, respectively.

FIG. 6 illustrates an alternative reactor which has feed lines 51, 52 and 53 connected thereto and an output line 54 for removing the reaction mixture therefrom. Inside the reactor 50 is a heat exchanger 55 which comprises a condensate header 56 in the lower portion of the reactor and an upper header 58 in the upper portion of the reactor. Conduits 58 interconnect the lower and upper headers. A heat exchange medium is contained within the headers and conduits of the heat exchange means. Optionally, an input line 59 for supplying a heat exchange medium is provided to the upper header 57 and an output line for removing heat exchange medium provided from lower condensate header 56.

In the embodiment where imput and output lines 59 and 60 are not provided, the heat exchange means 55 comprises a closed system consisting of headers 56 and 57 and conduits 58 having a heat exchange medium therein. Heat of reaction at the lower portion of the reactor is transferred to the heat exchange medium in header 56 and is preferably converted into latent heat. That is, in the event that the heat exchange medium is steam, the heat of reaction at the lower portion of the reactor converts condensate into steam at the lower portion of the heat exchange means. The heated steam then passes upwardly through conduits 58, as does the reaction product in the reactor. During the upward flow, heat from the steam is transferred to the reaction product and the steam, after being spent, becomes condensate and passes through conduits 58 back to condensate header 56 in the lower portion of the reactor. In this manner, the reaction product is heated at the upper portions of the reactor in an efficient and simple manner.

Optionally, the spent heat exchange medium can be removed from the upper header 57 and re-circulated back to the condensate heater 56 by external piping. A still further alternative is to supply a heated heat exchange medium to the upper header 57, the heat exchange medium being forced downwardly through conduits 58 to condensate header 56 and then removed from the system via conduit 60. This is an opened type system, whereas the preceding embodiments are closed type systems.

Another alternative is to remove spent heat exchange medium from the upper portion of the heat exchange means and to charge fresh heat exchange to the lower portion of the heat exchange means.

Thus, with the reactor of FIG. 6, a liquid heat exchange medium is vaporized in the bottom section of the heat exchanger located in a lower portion of the reactor, by the heat of reaction generated by the reactants fed into the reactor via lines 51–53. As the heated heat exchange medium passes to an upper portion of the system, its heat is transferred to the rising and cooling reactants and is eventually condensed in the upper section of the reactor. The condensate may be refluxed either internally (via conduits 58) or externally, or may be removed from the system and fresh heat medium supplied to the system. Steam and other conventional heat exchange media can be used.

I claim:

1. In a urea synthesis process wherein fluid NH$_3$, fluid CO$_2$ and an aqueous solution comprising ammonium carbamate are contacted at elevated pressure and elevated temperature to form a total urea synthesis mixture in a urea synthesis reactor to form urea, the improvement which comprises charging reactor feed streams of fluid NH$_3$, fluid CO$_2$ and an aqueous solution comprising ammonium carbamate to a lower portion of said reactor having an indirect heat exchange means positioned therein which extends from the lower portion to the upper portion of the reactor, said heat exchange means including a heat exchange medium and including a first header positioned in the upper portion of the reactor, a second header positioned in the lower portion of the reactor and conduit means in said reactor interconnecting said headers for passing heat exchange medium therebetween, imparting heat of reaction of said NH$_3$, CO$_2$ and ammonium carbamate mixture to said heat exchange medium in said second header at the lower portion of said reactor, and passing the resulting reaction mixture and said heat exchange medium to the upper portion of said reactor, said heat exchange medium being so passed through said conduit means to said first header, whereby heat of said heat exchange medium is transferred to said reaction mixture as it is passed from the lower portion to the upper portion of said reactor.

2. The process of claim 1, wherein said header positioned in the upper portion of the reactor contains means for supplying said heat exchange medium to said heat exchange means.

3. The process of claim 1, wherein said second header contains means for removing said heat exchange medium from said heat exchange means.

4. The process of claim 1, wherein the heat exchange medium is subsequently passed downwardly to the lower portion of the heat exchange means inside the reactor whereby it is reheated.

5. The system of claim 1, wherein spent heat exchange medium is removed from the first header of the heat exchange means and is returned to the second header of the heat exchange by means outside the reactor.

6. The process of claim 1, wherein spent heat exchange medium is removed from the first header and from the reactor and fresh heat exchange medium is charged to the second header within the reactor.

7. The process of claim 1, wherein the $NH_3$ to $CO_2$ molar ratio of the total urea sythesis mixture formed in the lower portion of said reactor is from about 2.8 to about 7 to 1.

* * * * *

UNITED STATES PATENT AND TRADEMARK OFFICE
CERTIFICATE OF CORRECTION

PATENT NO. : 4,088,685
DATED : May 9, 1978
INVENTOR(S) : IVO MAVROVIC

It is certified that error appears in the above–identified patent and that said Letters Patent are hereby corrected as shown below:

Column 11, line 43: replace "header 58" with ---header 57---.

Signed and Sealed this

Twenty-sixth Day of February 1980

[SEAL]

Attest:

SIDNEY A. DIAMOND

Attesting Officer     Commissioner of Patents and Trademarks